(12) United States Patent
Rahman et al.

(10) Patent No.: US 7,122,553 B2
(45) Date of Patent: Oct. 17, 2006

(54) LIPOSOMAL FORMULATION OF IRINOTECAN

(75) Inventors: Aquilur Rahman, Potomac, MD (US); Imran Ahmad, Wadsworth, IL (US)

(73) Assignee: NeoPharm, Inc., Waukegan, IL (US)

( * ) Notice: Subject to any disclaimer, the term of this patent is extended or adjusted under 35 U.S.C. 154(b) by 0 days.

(21) Appl. No.: 10/717,378

(22) Filed: Nov. 19, 2003

(65) Prior Publication Data

US 2005/0019387 A1   Jan. 27, 2005

Related U.S. Application Data

(63) Continuation of application No. PCT/US02/16844, filed on May 29, 2002.

(60) Provisional application No. 60/294,285, filed on May 29, 2001.

(51) Int. Cl.
*A61K 9/127* (2006.01)
*A61K 31/436* (2006.01)
*A61K 47/14* (2006.01)
*C07D 491/22* (2006.01)

(52) U.S. Cl. .................. 514/283; 424/450; 514/786

(58) Field of Classification Search ............... 424/450; 514/283, 786; 546/48
See application file for complete search history.

(56) References Cited

U.S. PATENT DOCUMENTS

| | | | |
|---|---|---|---|
| 3,993,754 A | 11/1976 | Rahman et al. | 514/12 |
| 4,008,209 A | 2/1977 | Fujino et al. | 530/313 |
| 4,016,100 A | 4/1977 | Suzuki et al. | 264/43 |
| 4,115,544 A | 9/1978 | Shell | 514/10 |
| 4,224,179 A | 9/1980 | Schneider | 264/4.6 |
| 4,229,360 A | 10/1980 | Schneider et al. | 264/4.6 |
| 4,235,871 A | 11/1980 | Papahadjopoulos et al. | 424/450 |
| 4,263,428 A | 4/1981 | Apple et al. | 536/6.4 |
| 4,311,712 A | 1/1982 | Evans et al. | 514/773 |
| 4,348,384 A | 9/1982 | Horikoshi et al. | 424/450 |
| 4,370,349 A | 1/1983 | Evans et al. | 424/365 |
| 4,396,630 A | 8/1983 | Riedl et al. | 424/365 |
| 4,411,894 A | 10/1983 | Schrank et al. | 514/221 |
| 4,419,348 A | 12/1983 | Rahman et al. | 514/34 |
| 4,473,692 A | 9/1984 | Miyasaka et al. | 546/48 |
| 4,515,736 A | 5/1985 | Deamer | 424/1.21 |
| 4,522,803 A | 6/1985 | Lenk et al. | 424/1.21 |
| 4,545,880 A | 10/1985 | Miyasaka et al. | 204/157.71 |
| 4,610,868 A | 9/1986 | Fountain et al. | 424/1.1 |
| 4,721,612 A | 1/1988 | Janoff et al. | 424/1.21 |
| 4,812,312 A | 3/1989 | Lopez-Berestein et al. | 424/417 |
| 4,857,319 A | 8/1989 | Crowe et al. | 424/94.1 |
| 4,952,408 A | 8/1990 | Rahman | 424/450 |
| 4,981,968 A | 1/1991 | Wall et al. | 544/361 |
| 5,003,097 A | 3/1991 | Beaucage et al. | |
| 5,023,087 A | 6/1991 | Yau-Young | 424/450 |
| 5,077,057 A | 12/1991 | Szoka, Jr. | 424/450 |
| 5,112,837 A | 5/1992 | Burrows et al. | 514/312 |
| 5,145,684 A | 9/1992 | Liversidge et al. | 424/489 |
| 5,162,532 A | 11/1992 | Comins et al. | 546/48 |
| 5,187,167 A | 2/1993 | Hughes | 514/259 |
| 5,247,089 A | 9/1993 | Comins et al. | 546/48 |
| 5,264,423 A | 11/1993 | Cohen et al. | |
| 5,276,019 A | 1/1994 | Cohen et al. | |
| 5,286,717 A | 2/1994 | Cohen et al. | |
| 5,352,789 A | 10/1994 | Hinz | 546/48 |
| 5,389,377 A | 2/1995 | Chagnon et al. | 424/450 |
| 5,391,745 A | 2/1995 | Danishefsky et al. | 546/48 |
| 5,415,867 A | 5/1995 | Minchey et al. | 424/450 |
| 5,422,344 A | 6/1995 | Priel et al. | 514/50 |
| 5,424,073 A | 6/1995 | Rahman et al. | 424/450 |
| 5,447,936 A | 9/1995 | Hausheer et al. | 514/283 |
| 5,468,859 A | 11/1995 | Fortunak et al. | 546/48 |
| 5,475,108 A | 12/1995 | Comins et al. | 546/41 |
| 5,496,830 A | 3/1996 | Shapiro et al. | 514/283 |
| 5,504,102 A | 4/1996 | Agharkar et al. | 514/449 |
| 5,527,913 A | 6/1996 | Hinz | 546/48 |
| 5,541,327 A | 7/1996 | Danishefsky et al. | 546/48 |
| 5,552,154 A | 9/1996 | Giovanella et al. | 424/449 |
| 5,552,156 A | 9/1996 | Burke | 424/450 |
| 5,560,923 A | 10/1996 | Rahman et al. | 424/450 |
| 5,608,066 A | 3/1997 | Hinz | 546/48 |
| 5,616,334 A | 4/1997 | Janoff et al. | 424/404 |
| 5,622,959 A | 4/1997 | Priel et al. | 514/283 |
| 5,648,090 A * | 7/1997 | Rahman et al. | 424/450 |
| 5,651,986 A | 7/1997 | Brem et al. | 424/484 |
| 5,652,244 A | 7/1997 | Giovanella et al. | 514/283 |
| 5,665,710 A | 9/1997 | Rahman et al. | 514/44 |
| 5,674,873 A | 10/1997 | Hausheer et al. | 514/283 |
| 5,674,874 A | 10/1997 | Hausheer et al. | 514/283 |

(Continued)

FOREIGN PATENT DOCUMENTS

EP         0 288 255 A2      10/1988

(Continued)

OTHER PUBLICATIONS

Okuno et al. Complete Regression of Xenografted Human carcinomas. by Camptothecin Analogue-Carboxymethyl Dextran Conjugate (T-0128). Cancer Research. Jun. 1, 2000. vol. 60, pp. 2988-2995.*

(Continued)

*Primary Examiner*—Jeffrey Edwin Russel
(74) *Attorney, Agent, or Firm*—DLA Piper Rudnick Gray Cary US LLP

(57) ABSTRACT

The present invention is for novel compositions and methods for treating cancer, particularly, for treating cancer in mammals and more particularly in humans. The therapeutic compositions of the present invention include liposome entrapped irinotecan in which the liposome can contain any of a variety of neutral or charged liposome-forming compounds and cardiolipin. The liposomes of the present invention can be either multilamellar vesicles and unilamellar vesicles, as desired.

24 Claims, No Drawings

U.S. PATENT DOCUMENTS

| | | | |
|---|---|---|---|
| 5,726,181 A | 3/1998 | Hausheer et al. | 514/283 |
| 5,736,156 A | 4/1998 | Burke | 424/450 |
| 5,759,767 A | 6/1998 | Lakowicz et al. | 435/4 |
| 5,776,486 A | 7/1998 | Castor et al. | 424/450 |
| 5,776,743 A | 7/1998 | Frisch | 435/6 |
| 5,786,344 A * | 7/1998 | Ratain et al. | 514/100 |
| 5,834,012 A | 11/1998 | Perez-Soler et al. | 424/450 |
| 5,837,282 A | 11/1998 | Fenske et al. | 424/450 |
| 5,837,673 A | 11/1998 | Tsujihara et al. | 514/2 |
| 5,846,565 A | 12/1998 | Brem et al. | 424/486 |
| 5,859,022 A | 1/1999 | Hausheer et al. | 514/283 |
| 5,859,023 A | 1/1999 | Hausheer et al. | 514/283 |
| 5,880,133 A | 3/1999 | Hausheer et al. | 514/283 |
| 5,882,679 A | 3/1999 | Needham | 424/450 |
| 5,889,017 A | 3/1999 | Giovanella et al. | 514/283 |
| 5,900,419 A | 5/1999 | Hausheer et al. | 514/283 |
| 5,916,596 A | 6/1999 | Desai et al. | 424/489 |
| 5,948,750 A | 9/1999 | Garsky et al. | 514/2 |
| 5,955,467 A | 9/1999 | Hausheer et al. | 514/283 |
| 5,958,937 A | 9/1999 | Hausheer et al. | 514/283 |
| 5,962,216 A | 10/1999 | Trouet et al. | 435/4 |
| 5,965,519 A | 10/1999 | Yatvin et al. | |
| 5,972,955 A | 10/1999 | Duvvuri et al. | 514/283 |
| 5,985,888 A | 11/1999 | Wall et al. | 514/283 |
| 5,998,426 A | 12/1999 | Bedeschi et al. | 514/283 |
| 6,015,901 A | 1/2000 | Kawaguchi et al. | 546/89 |
| 6,046,159 A | 4/2000 | Hausheer et al. | 514/2 |
| 6,056,973 A | 5/2000 | Allen et al. | 424/450 |
| 6,057,361 A | 5/2000 | Hausheer et al. | 514/460 |
| 6,066,645 A | 5/2000 | Hausheer et al. | 514/283 |
| 6,069,134 A | 5/2000 | Roth et al. | 514/44 |
| 6,090,407 A | 7/2000 | Knight et al. | 424/450 |
| 6,096,336 A | 8/2000 | Cao et al. | 424/450 |
| 6,126,965 A | 10/2000 | Kasid et al. | |
| 6,146,659 A * | 11/2000 | Rahman | 424/450 |
| 6,183,958 B1 | 2/2001 | Stanton, Jr. | |
| 6,214,388 B1 | 4/2001 | Benz et al. | 424/812 |
| 6,291,175 B1 | 9/2001 | Sévigny et al. | |
| 6,291,676 B1 | 9/2001 | Burke et al. | 546/48 |
| 6,333,314 B1 | 12/2001 | Kasid et al. | |
| 6,355,268 B1 | 3/2002 | Slater et al. | 424/450 |
| 6,368,797 B1 | 4/2002 | Schappert | |
| 6,395,481 B1 | 5/2002 | Di Rienzo et al. | |
| 6,407,117 B1 * | 6/2002 | Bouscarel et al. | 514/283 |
| 6,461,637 B1 | 10/2002 | Rahman | 424/450 |
| 6,475,736 B1 | 11/2002 | Stanton, Jr. et al. | |
| 6,500,650 B1 | 12/2002 | Stanton, Jr. et al. | |
| 6,537,759 B1 | 3/2003 | Stanton, Jr. et al. | |
| 6,548,071 B1 | 4/2003 | Cherian | 424/400 |
| 6,559,129 B1 | 5/2003 | Kasid et al | |
| 6,573,049 B1 | 6/2003 | Schappert | |
| 6,582,923 B1 | 6/2003 | Stanton, Jr. et al. | |
| 6,610,492 B1 | 8/2003 | Stanton, Jr. et al. | |
| 6,664,062 B1 | 12/2003 | Stanton, Jr. | |
| 6,740,335 B1 | 5/2004 | Moynihan et al. | 424/450 |
| 2002/0103141 A1 | 8/2002 | McKearn et al. | 514/43 |
| 2002/0119990 A1 | 8/2002 | Madden et al. | 514/283 |
| 2002/0150943 A1 | 10/2002 | Stanton, Jr. et al. | |
| 2003/0059465 A1 | 3/2003 | Unger et al. | 424/465 |
| 2003/0073123 A1 | 4/2003 | Shen et al. | |
| 2003/0215489 A1 | 11/2003 | Kasid et al. | |
| 2003/0215492 A1* | 11/2003 | Ahmad et al. | 424/450 |
| 2003/0219476 A1 | 11/2003 | Ahmad et al. | |
| 2003/0225023 A1 | 12/2003 | Kasid et al. | |
| 2003/0228317 A1 | 12/2003 | Gokhale et al. | |
| 2003/0229040 A1 | 12/2003 | Kasid et al. | |
| 2004/0005603 A1 | 1/2004 | Kasid et al. | |
| 2004/0009229 A1 | 1/2004 | Unger et al. | 424/486 |
| 2004/0082771 A1 | 4/2004 | Kasid et al. | |
| 2004/0106571 A1 | 6/2004 | Kasid et al. | |
| 2004/0115714 A1 | 6/2004 | Kasid et al. | |
| 2004/0248218 A1 | 12/2004 | Kasid et al. | |
| 2005/0002918 A1 | 1/2005 | Strauss et al. | |
| 2005/0019387 A1 | 1/2005 | Rahman et al. | |
| 2005/0148528 A1 | 7/2005 | Gately | |
| 2005/0153297 A1 | 7/2005 | Ahmad et al. | |
| 2005/0181037 A1 | 8/2005 | Ahmad et al. | |
| 2005/0202074 A9 | 9/2005 | Rahman | |
| 2005/0238706 A1 | 10/2005 | Ahmad et al. | |
| 2005/0249795 A1 | 11/2005 | Zhang et al. | |
| 2005/0266068 A1 | 12/2005 | Ahmad et al. | |
| 2005/0277611 A1 | 12/2005 | Ahmad et al. | |

FOREIGN PATENT DOCUMENTS

| | | |
|---|---|---|
| EP | 1 352 970 A1 | 10/2003 |
| SU | 629927 A | 10/1978 |
| SU | 1186212 A | 10/1985 |
| WO | WO 83/03383 A1 | 10/1983 |
| WO | WO 86/01103 A1 | 2/1986 |
| WO | WO 93/18751 A1 | 9/1993 |
| WO | WO 95/08386 A1 | 4/1995 |
| WO | WO 95/08986 | 4/1995 |
| WO | WO 96/11669 A1 | 4/1996 |
| WO | WO 98/17256 A1 | 4/1998 |
| WO | WO 98/43095 A | 10/1998 |
| WO | WO 99/13816 A2 | 3/1999 |
| WO | WO 99/51202 A2 | 10/1999 |
| WO | WO 00/01366 A | 1/2000 |
| WO | WO 00/23052 A1 | 4/2000 |
| WO | WO 00/50639 A | 8/2000 |
| WO | WO 00/52210 A | 9/2000 |
| WO | WO 01/53460 A | 7/2001 |
| WO | WO 01/70220 A | 9/2001 |
| WO | WO 02/00168 A2 | 1/2002 |
| WO | WO 02/32400 A | 4/2002 |
| WO | WO 02/059337 A | 8/2002 |
| WO | WO 02/081639 A | 10/2002 |
| WO | WO 02/081640 A | 10/2002 |
| WO | WO 02/081641 A | 10/2002 |
| WO | WO 02/081642 A | 10/2002 |
| WO | WO 02/088714 A | 11/2002 |
| WO | WO 03/013536 A | 2/2003 |
| WO | WO 03/013537 A | 2/2003 |
| WO | WO 03/018018 A | 3/2003 |
| WO | WO 03/030864 A1 | 4/2003 |
| WO | WO 03/039600 A | 5/2003 |
| WO | WO 02/058622 A2 | 8/2003 |
| WO | WO 03/070221 A | 8/2003 |
| WO | WO 03/099213 A | 12/2003 |
| WO | WO 03/099830 A | 12/2003 |
| WO | WO 03/102011 A | 12/2003 |
| WO | WO 03/103596 A2 | 12/2003 |
| WO | WO 04/017940 A3 | 3/2004 |
| WO | WO 2004/017944 A | 3/2004 |
| WO | WO 04/035032 A2 | 4/2004 |
| WO | WO 2004/035523 A | 4/2004 |
| WO | WO 2004/039817 A | 5/2004 |
| WO | WO 2004/062569 A | 7/2004 |
| WO | WO 2004/069224 A | 8/2004 |
| WO | WO 2004/071466 A | 8/2004 |
| WO | WO 2004/087758 A | 10/2004 |
| WO | WO 2005/000266 A | 1/2005 |
| WO | WO 2005/000318 A | 1/2005 |
| WO | WO 2005/042028 A | 5/2005 |
| WO | WO 2005/067632 A | 7/2005 |

OTHER PUBLICATIONS

Y. Sadzuka, "Effective Prodrug Liposome and Conversion to Active Metabolite," *Current Drug Metabolism*, 1(1), 31-48 (2000).

Sadzuka, "Effect of liposomalization on the antitumor activity, side-effects and tissue distribution of CPT-11," *Cancer Letters*, 127, 99-106 (1998).

U.S. Appl. No. 11/061,044, filed Feb. 18, 2005, Ahmad et al.

U.S. Appl. No. 60/247,306, filed Nov. 9, 2000, Rahman et al.
U.S. Appl. No. 60/294,285, filed May 29, 2001, Rahman et al.
U.S. Appl. No. 60/404,668, filed Aug. 20, 2002, Rahman et al.
Akhtar et al., *Journal of Controlled Release*, 22: 47-56 (1992).
Allen et al., *Biochimica et Biophysica Acta*, 981(1): 27-35 (May 19, 1989).
Allen et al., *Cancer Research*, 52: 2431-2439 (May 1, 1992).
Blume et al., *Biochimica et Biophysica Acta*, 1029(1): 91-97 (Nov. 2, 1990).
Burke et al., *Journal of the American Chemical Society*, 114(21): 8318-8319 (Oct. 7, 1992).
Burke et al., *Biochemistry*, 32(20): 5352-5364 (May 25, 1993).
Burris et al., *Journal of the National Cancer Institute*, 84(23), No. 23: 1816-1820 (Dec. 2, 1992).
Cavaletti et al., *Toxicology Letters*, 118: 103-107 (2000).
Cecil Textbook of Medicine, 15$^{th}$ Edition, vol. 1: 396-399, 475-479 and 817-821 (1997).
Chakrabarti et al., *Biochimica et Biophysica Acta*, 1108(2): 233-239 (1992).
Clements et al., *Cancer Chemother Pharmacol*, 44: 411-416 (1999).
Crommelin et al., *Pharmaceutical Research*, 4: 159-163 (Jul. 1984).
Crowe et al., *Archives of Biochemistry And Biophysics*, 220(2): 477-484 (Feb. 1983).
Crowe et al., *Archives of Biochemistry And Biophysics*, 232(1): 400-407 (Jul. 1984).
Crowe et al., *Biochimica et Biophysica*, 769: 151-159 (1984).
Crowe et al., *Biochimica et Biophysica*, 769: 141-150 (1984).
Crowe et al., *Archives Biochemistry And Biophysics*, 242(1): 240-247 (Oct. 1985).
Daoud et al., *Cancer Research*, 49: 2661-2667 (1989).
Deamer et al., *Liposomes*, (Ostro, eds), 27-51 (Marcel Dekker, Inc., New York, NY, 1983).
Druckmann et al., *Biochimica et Biophysica Acta*, 980(2): 381-384 (1989).
Emerson et al., *Cancer Research*, 55: 603-609 (1995).
Emerson et al., *Pharmaceutical Science & Technology Today*, 3(6): 205-209 (Jun. 2000).
Erickson-Miller et al., *Cancer Chemother Pharmacol*, 39: 467-472 (1997).
Fan et al., *Cancer Research*, 50: 3619-3626 (Jun. 15, 1990).
Forssen et al., *Biochemical And Biophysical Research Communications*, 91(4): 1295-1301 (Dec. 28, 1979).
Forssen et al., *Cancer Research*, 43: 546-550 (1983).
Forssen et al., *Cancer Research*, 52: 3255-3261 (1992).
Fry et al., *Analytical Biochemistry*, 90: 809-815 (1978).
Gabizon et al., *Proc. Natl. Acad. Sci. USA*, 85: 6949-6953 (Sep. 1988).
Gabizon et al., *Cancer Research*, 50: 6371-6378 (Oct. 1, 1990).
Garcia-Carbonero et al., *Clinical Cancer Research*, 8: 641-661 (Mar. 2002).
Giovanella et al., *Science*, 246(4933): 1046-1048 (Nov. 24, 1989).
Giovanella et al., *Cancer Research*, 51: 3052-3055 (Jun. 1, 1991).
Gokhale et al., *British Journal of Cancer*, 74: 43-48 (1996).
Green Cross Corporation, *Chemical Abstracts.*, 97:11851g: (1982).
Gregoriadis et al., *The New England Journal of Medicine*, 295(12): 704-710 (1976).
Grochow et al., *Drug Metabolism and Disposition*, 20(5): 706-713 (1992).
Guichard et al., *Clinical Cancer Research*, 4: 3089-3094 (Dec. 1998).
Hardman et al., *Anticancer Research*, 19: 2269-2274 (1999).
Hardman et al., *British Journal of Cancer*, 81(3): 440-8 (Oct. 1999).
Hillery, *Advanced Drug Delivery Reviews*, 24(2 & 3): 345-363 (1997).
Hong et al., *J. Med. Chem.*, Computer Search Listing Abstract (May 1990).
Hong et al., *Cancer Research*, Computer Search Listing Abstract (Jul. 15, 1990).
Hsiang et al., *Cancer Research*, 48: 1722-1726 (Apr. 1, 1988).
Huang et al., *Cancer Research*, 52: 5135-5143 (Oct. 1, 1992).
Innocenti et al., *Drug Metabolism & Dispositions*, 29(4): 596-600 (2001).
Janoff et al., *Journal of Liposome Research*, 3(3): 451-471 (1993).

Jansen et al., *International Journal of Cancer*, 70(3): 335-340 (Jan. 27, 1997).
Jett et al., *Methods in Enzymology*, 141: 459-466 (1983).
Kawato et al., *Cancer Research*, 51(16): 4187-91 (Aug. 15, 1991).
Kawato et al., *Cancer Chemotherapy and Pharmacology*, 28(3): 192-198 (1991).
Killion et al., *Journal of the National Cancer Institute*, 81(18): 1387-1392 (Sep. 6, 1989).
Knotting et al., *Cancer-Chemother-Pharmacol.*, Computer Search Listing Abstract (1992).
LASIC, *American Scientist*, 80(1): 20-31 (Jan.-Feb. 1992).
LASIC, *Nature*, 355(6357): 272-280 (Jan. 16, 1992).
Lavelle et al., *Seminars in Oncology* 23(1) Suppl.3: 11-20 (Feb. 1996).
Lundberg, *Anti-Cancer Drug Design*, 13: 453-461 (1998).
Machida et al., *Journal of Controlled Release*, 66: 159-175 (2000).
Machy et al., *Biochimica et Biophysica Acta.*, 730: 313-320 (1983).
Madden et al., *Biochimica et Biophysica Acta.*, 817: 67-74 (1985).
Madden et al., *Chemistry and Physics of Lipids*, 53: 37-46 (1990).
Madden et al., *Proc. Of ASCO*, 17:abstract #754: (1998).
Margalit et al., *Journal of Controlled Release*, 17(3): 285-296 (1991).
Mathijssen et al., *Clinical Cancer Research*, 7: 2182-2194 (Aug. 2001).
Mayer et al., *Cancer Research*, 49: 5922-5930 (1989).
Mayer et al., *Biochimica et Biophysica Acta.*, 1025: 143-151 (1990).
McCabe et al., *Cancer Investigation*, 12(3): 308-313 (1994).
Monks et al., *Journal of the National Cancer Institute*, (83(11): 757-766 (Jun. 5, 1991).
Okuno et al., *Cancer Research*, 60: 2988-2995 (Jun. 1, 2000).
O'Leary et al., *Clinical Cancer Research*, 5: 181-187 (Jan. 1999).
Olitzki, *In vivo Procedures, Bibliotheca Microbiologica*, 9: 196-203 (1970).
Ormrod et al., *ADIS Drug Evaluation*, 58(3): 534-551 (1999).
Pagano, *Annual Review of Biophysics and Bioengineering*, 7: 435-468 (1978).
Palmisano et al., *Anal-Chem.*, Computer Listing Search Abstract, (May 1, 1989).
Pantazis et al., *Cancer Research*, 52: 3980-3987 (Jul. 15, 1992).
Papahadjopoulos et al., *Proc. Natl. Acad. Sci. USA*, 88: 11460-11464 (Dec. 1991).
Partearroyo et al., *FEBS Letters*, 302(2): 138-140 (May 1992).
Pejaver et al., *Drug Development and Industrial Pharmacy*, 13(15): 2633-2649 (1987).
Perez-Soler, *Cancer Treatment Reviews*, 16(2): 67-82 (Jun. 1989).
Perez-Soler et al., *Cancer Research*, 50: 4254-4259 (Jul. 15, 1990).
Pinnaduwage et al., *Biochemistry*, 31(11): 2850-2855 (Mar. 24, 1992).
Pizzolato et al., *Lancet*, 361: 2235-2242 (Jun. 28, 2003).
Potmesil et al., *DNA Topoisomerases Cancer, Chemical Abstract* 117(103,369): (1991).
Racker, *J. Membrane Biol.*, 10: 221-235 (1972).
Rahman et al., *Cancer Research*, 45: 796-803 (Feb. 1985).
Rahman et al., *J. of the Nat. Cancer Institute*, 81(23): 1794-1800 (Dec. 6, 1989).
Ratain et al., *Journal of Clinical Oncology*, 20(1): 7-8 (Jan. 1, 2002).
Rieger, *Pharmaceutical Dosage Forms Disperse System*, 1(8): 334-338 (1988).
Senior et al., *Biochimica et Biophysica Act*, 1070: 173-179 (1991).
Shelly et al., *Proc. Natl. Acad Sci. USA.*, 89: 9039-9043, (Oct. 1992).
Shulkin et al., *J. Microencapsultion*, 1(1): 73-80 (1984).
Storm et al., *Cancer Research*, 47: 3366-3372 (Jul. 1, 1987).
Sugarman et al., *1-Pharmacology, Chemical Abstract* No. 124:332078g, 124(25): 94 (1996).
Supersaxo et al., *Pharmaceutical Research*, 8(10): 1286-1291 (Oct. 1991).
Szoka et al., *Proc. Natl. Acad. Sci. USA*, 75(9): 4194-4198 (Sep. 1978).
Szoka, *Ann. Rev. Biophys. Bioeng.*, 9: 467-508 (1980).
Tardi et al., *Cancer Research*, 60: 3389-3393 (Jul. 1, 2000).
Thies et al., *Analytical Biochemistry*, 188: 65-71 (1990).

Thompson et al., *Biochimica et Biophysica Acta*, 1400: 301-319 (1998).
Topchieva et al., *Biomed-Sci.*, Computer Listing Search Abstract, (1991).
Tsyganenko et al., *Antibiotiki*, 28(8): 577-581 (1983).
Usov et al., *Bioorg-Khim*, Computer Listing Search Abstracts, (1991).
Vion-Dury et al., *J. Pharm. And Exp. Therapeutics*, 250(3): 1113-1119 (1989).
Wadkins et al., *Cancer Research*, 59(14): 3424-8 (Jul. 15, 1999).
Wall et al., *J. of the American Chem. Soc.*, 88(16): 3888-3890 (1966).
Weinstein, *Liposomes*, (Ostro eds), 277-338 (Marcel Dekker, Inc., New York, NY, 1983).
Williams et al., *J. Controlled Release*, 91: 167-172 (2003).
Woodle et al., *Methods in Enzymology*, 171: 193-217 (1989).
Wu et al., *Chemical Abstracts*, 99:163963z: (1983).
Yokoyama et al., *Cancer-Res.*, Computer Listing Search Abstract, (1991).
U.S. Appl. No. 09/354,109, filed Jul. 15, 1999, Kasid et al.
U.S. Appl. No. 09/930,283, filed Aug. 16, 2001, Kasid et al.
U.S. Appl. No. 10/056,210, filed Jan. 28, 2002, Kasid et al.
U.S. Appl. No. 10/239,598, filed Oct. 25, 2000, Rahman.
U.S. Appl. No. 10/680,313, filed Oct. 06, 2003, Kasid et al.
U.S. Appl. No. 60/041,192, filed Mar. 21, 1997, Kasid et al.
U.S. Appl. No. 60/241,069, filed Oct. 16, 2000, Rahman et al.
U.S. Appl. No. 60/264,062, filed Jan. 26, 2001, Kumar et al.
U.S. Appl. No. 60/281,779, filed Apr. 06, 2001, Kasid et al.
U.S. Appl. No. 60/281,780, filed Apr. 6, 2001, Kasid et al.
U.S. Appl. No. 60/281,785, filed Apr. 6, 2001, Kasid.
U.S. Appl. No. 60/281,796, filed Apr. 6, 2001, Kasid et al.
U.S. Appl. No. 60/314,959, filed Aug. 24, 2001, Rahman et al.
U.S. Appl. No. 60/332,477, filed Nov. 9, 2001, Strauss et al.
U.S. Appl. No. 60/371,116, filed Apr. 10, 2002, Kasid et al.
U.S. Appl. No. 60/371,126, field Apr. 10, 2002, Kasid et al.
U.S. Appl. No. 60/382,031, filed May 22, 2002, Gokhale et al.
U.S. Appl. No. 60/382,411, filed May 20, 2002, Gately.
U.S. Appl. No. 60/383,340, filed May 24, 2002, Ahmad et al.
U.S. Appl. No. 60/384,222, filed May 29, 2002, Ahmad et al.
U.S. Appl. No. 60/405,378, filed Aug. 23, 2002, Zhang et al.
U.S. Appl. No. 60/419,277, filed Oct. 16, 2002, Ahmad et al.
U.S. Appl. No. 60/429,285, filed Nov. 26, 2002, Ahmed et al.
U.S. Appl. No. 60/438,659, filed Jan. 7, 2003, Ahmad et al.
U.S. Appl. No. 60/444,958, filed Feb. 3, 2003, Zhang et al.
U.S. Appl. No. 60/446,895, filed Feb. 11, 2003, Bhamidipati et al.
U.S. Appl. No. 60/457,898, filed Mar. 26, 2003, Gately et al.
U.S. Appl. No. 60/467,331, filed May 2, 2003, Ahmad et al.
U.S. Appl. No. 60/472,664, filed May 22, 2003, Jamil et al.
U.S. Appl. No. 60/480,669, filed June 23, 2003, Jamil et al.
U.S. Appl. No. 60/495,260, filed Aug. 13, 2003, Jamil et al.
U.S. Appl. No. 60/514,658, filed Oct. 27, 2003, Ahmad et al.
Office Action mailed Dec. 30, 2005, in U.S. Appl. No. 10/424,258.
Ando et al., "UGT1A1 genotypes and glucuronidation of SN-38, the active metabolite of irinotecan," *Ann. Oncol.*, 9, 845-847 (1998).
Ando et al., "Polymorphisms of UDP-glucuronosyltransferase gene and irinotecan toxicity: a pharmacogenetic analysis," *Cancer Res. 60*, 6921-6926 (2000).
Bosma et al., "Bilirubin UDP-glucuronosyltransferase 1 is the only relevant bilirubin glucuronidationg isoform in man," *J. Biol. Chem. 269*, 17960-17964 (1994).
Bosma et al., "The genetic basis of the reduced expression of bilirubin UDP-glucuronosylterease 1 in Gilbert's," *New Engl. J. Med. 333*, 1171-1175 (1995).
Cersosimo et al., "A new antineoplastic agent for the management of colorectal cancer," *Ann. Pharmacother* 32:1324-1333, (1998).
Drummond et al., "Optimizing Liposomes for Delivery of Chemotherapeutic Agents to Solid Tumors," *Pharmacol. Rev. 51*, 691-743 (1999).
Fishman et al., "Phase I study of Liposomal SN-38 (LE-SN38) in Patients With Advanced Cancer: Pharmacogenomics and Pharmacokinetics," *AARC-NCI-EORTC International Conference on Molecular Targents and Cancer Therapeutics* (Boston, MA), Abstract B250 (Nov. 2003).

Fishman et al., "Phase I study of liposome encapsulated mitoxantrone (LEM) in patients with advanced cancers," *Ann. Oncol. 13* (Suppl. 5), 23 (2002).
Gilbert et al., "Phase I study of 9-nitrocamptothecin (9-NC) liposome aerosol for the treatment of primary and metastatic cancer to the lungs: effect of dose escalation on bronchoalveolar lavage (BAL) and plasma drug levels," *Proc. Am. Assoc. Cancer res., 43*, 430 (Abstract 2138) (2002).
Gupta et al., "Metabolic fate of irinotecan in humans: correlationof glucuronidation with diarrhea," *Cancer Res. 54*, 3723-3725 (1994).
Gutberlet et al., "Cardiolipin, α-D-glucopyranosyl, and L-lysylcardiolipin from Gram-positive bacteria: FAB MS, monifilm and X-ray powder diffraction studies," *Biochim. Biophys, Acta, 463*, 307-322 (2000).
Hecht, "Gastrointestinal toxicity of irinotecan," *Oncology 12*, 72-78 (1998).
Hsiang et al., "Arrest of replication forks by drug-stabilied topoisomerase I-DNA cleavable complexes as a mechanism of cell killing by camptothecin," *Cancer Res. 49*, 5077-5082 (1989).
Hsiang et al., "Camptothecin induces protein-linked DNA breaks via mammalian DNA topoisomerase I," *J. Biol. Chem. 260*, 14873-14878 (1985).
Innocenti et a., "UGT1A1 *28 polymorphism is a predictor of neutropenia in irinotecan chemotherapy," *Proc. Am. Soc. Clin. Oncol., 22*, 124 (Abstract 495) (2003).
Iyer et al., "Genetic predisposition to the metabolism of irinotecan (CPT-11). Role of uridine diphosphate glucuronosyltransferase isoform 1A1 in the glucuronidation of its active metabolite (SN-38) in human liver microsomes," *J Clin Invest 101*:847-854, (1998).
Iyer et al., "Phenotype-genotype correlation of in vitro SN-38 (active metabolite of irinotecan) and bilirubin glucuronidation in human liver tissue with UGT1 A1 promoter polymorphism," *Clin. Pharmacol. Ther., 65*, 576-582 (1999).
Iyer et al., "UGT1A1 *28 polymorphism as a determinant of irinotecan disposition and toxicity," *Pharmacogenetics, 2*, 43-47 (2002).
Kehrer et al., "Factors involved in prolongation of the terminal disposition phase of SN-38: clinical and experimental studies," *Clin. Cancer Res., 6*, 3451-3458 (2000).
Knight et al., "Anticancer effect of 9-nitrocamptothecin liposome aerosol on human cancer xenografts in nude mice," *Cancer Chemother. Pharmacol., 44*, 177-186 (1999).
Kraut et al., "Pharmacogenomic and pharmacokinetic assessment of liposome encapsulated SN-38 (LE-SN38) in advanced cancer patients," presented at ASCO (American Society of Clinical Oncology), New Orleans, LA Jun. 5-8, 2004, Abstract 2501 (Jun. 5, 2004).
Kunimoto et al., "Antitumor activity of 7-ethyl-10-[4-(1-piperidino)-1-piperidino]carbonyloxy-camptothecin, a novel water soluble derivative of camptothecin, against murine tumors," *Cancer Res. 47*: 5944-5947, (1987).
Lampe et al., "UDP-glucuronosyltransferase (UGT1A1 *28 and UGT1A6*2) polymorphisms in Caucasians and Asians: relationships to serum bilirubin concentrations," *Pharmacogenetics, 9*, 341-349 (1999).
Lavelle et al., "Preclinical evaluation of CPT-1 1 and its active metabolite SN-38," *Semin. Oncol., 23*, 11-20 (1996).
Mathussen et al., "Impact of body-size measures on irinotecan clearance: alternative dosing recommendations," *J. Clin. Oncol., 20*, 81-87 (2002).
Monaghan et al., "Genetic variation in bilirubin UPD-glucuronosyltransferase gene promoter and Gilbert's syndrome," *Lancet, 347*, 578-581 (1996).
O'Leary et al., "Camptothecins: a review of their development and schedules of administration," *Eur. J. Cancer., 34*, 1500-1508 (1998).
Osborne, "Nastech licenses RNAi patents to boost tight junctions work," *BioWorld today*, 15(21), 1, 6 (Feb. 3, 2004).
Pfizer, Inc., Package insert for Camptosar® (Jul. 2005).
Pitot et al, "Phase I dose-finding and pharmacokinetic trial of irinotecan hydrochloride (CPT-11) using a once-every-three-week dosing schedule for patients with advanced solid tumor malignancy," *Clin Cancer Res., 6*, 2236-2244 (2000).

Rainier et al., "Phase transition characteristics of diphosphatidylglycerol (cardiolipin) and stereoisomeric phosphatidyldiacylglycerol bilayers: mono-and divalent metal ion effects," *Biochim. Biophys, Acta, 558* , 187-198 (1979).

Rivory et al, "Kinetics of the in vivo interconversion of the carboxylate and lactone forms of irinotecan (CPT-11) and of its metabolite SN-38 in patients," *Cancer Res. 54* : 6330-6333, (1994).

Rivory et al, "Pharmacokinetic interrelationships of irinotecan (CPT-11) and its-three major plasma metabolites in patients enrolled in phase I/II trials," *Clin. Cancer Res., 3* , 1261-1266 (1997).

Rivory, "Metabolism of CPT-11 impact on activity," *Ann. N. Y. Acad. Sci., 922* , 205-215 (2000).

Rothenberg, "Topoisomerase I inhibitors: review and update, " *Ann. Oncol.* 8:837-855, (1997).

Sanghani et al., "Carboxylesterases expressed in human colon tumor tissue and their role in CPT-11 hydrolysis," *Clin. Cancer Res., 9* (13), 4983-4991 (Oct. 15, 2003).

Sasaki et al., "Pharmacological correlation between total drug concentration and lactones of CPT-11 and SN-38 in patients treated with CPT-11," *Cancer Res., 86* , 111-116 (1995).

Schaeppi et al., "Toxicity of camptothecin (NSC-100880)," *Cancer Chemother. Rep., 5* , 25-36 (1974).

Slatter et al., "Pharmacokinetics, metabolism and excretion of irinotecan (CPT-11) following iv infusion of [14C]CPT-11 in cancer patients," *Drug Metab. Dispos., 28* , 423-433 (2000).

Strassburg et al., "Jaundice, genes and promoters," *J. Hepatol., 33* , 467-479 (2000).

Takimoto et al., "The captothecins," *The camptothecins. Cancer chemotherapy and biotherapy* , 2nd ed. (Chabner et al., eds.), Chapter 19, 463-484 (Lippincott-Raven, Philadelphia, PA, 1996).

Treat et al., "Phase I trial in advanced malignancies with liposome encapsulated paclitaxel (LEP)," *Clin. Cancer Res., 6* , 4492s (2000).

Vanhoefer et al., "Irinotecan in the treatment of colorectal cancer: clinical overview," *J. Clin.Oncol., 19* , 1501-1518 (2001).

Vaughn et al., "A phase I study of a new liposome encapsulated doxorubicin (LED) formulation in advanced malignancies," *Proc. Am. Soc. Clin. Oncol., 19* (23), 1a (Abstract 892) (1999).

Wadler et al., "Recommended guidelines for the treatment of chemotherapy-induced diarrhea," *J. Clin. Oncol., 16* , 3169-3178 (1998).

Wasserman et al., "Severe CPT-1 1 toxicity in patients with Gilbert's syndrome: two case reports," *Ann. Oncol., 8* , 1049-1051 (1997).

\* cited by examiner

LIPOSOMAL FORMULATION OF IRINOTECAN

BACKGROUND OF THE INVENTION

This invention pertains to formulations and methods for making camptothecin-containing liposomes that minimize or reduce multidrug resistance when administered to humans. The invention is also directed to the use of these liposomes in the treatment of disease, particularly cancer.

DESCRIPTION OF THE BACKGROUND

Camptothecin molecules and irinotecan in particular are potent therapeutic agents for the treatment of cancer. Their metabolite, SN-38, is thought to bind to the enzyme topoisomerase I, the enzyme responsible for relieving torsional strain in DNA. The bound metabolite is thought to be cytotoxic because it blocks religation of the single-strand breaks induced by topoisomerase-I and thereby disrupts the DNA strands which, are not then sufficiently repaired.

The metabolic conversion of camptothecins to SN-38 occurs primarily in the liver and is thought to involve carboxylesterase-mediated cleavage of the carbamate bond between the camptothecin moiety and a dipiperidino side chain. Subsequently, this derivative undergoes conjugation to form the glucuronide metabolite.

Camptothecins are exceedingly insoluble in aqueous solutions. Despite their lack of solubility in water, they also have a low affinity for lipid membranes from which they tend to precipitate into aqueous phase. These solubility characteristics interfere with their use as therapeutic agents.

Irinotecan hydrochloride injection is a first-line therapy for the treatment of patients with metastatic (widespread) colorectal cancer in conjunction with fluorouracil [5FU] and leucovorin. Significant improvements have been observed in objective tumor response rates, time to tumor progression, and prolongation of survival for the regimen of irinotecan hydrochloride and 5FU/leucovorin compared with 5FU/leucovorin alone. Moreover, the addition of irinotecan to the treatment regimen does not interfere with the quality of life of patients. In addition to its current colorectal cancer indication, irinotecan may also find use in adjuvant treatment option (with 5FU/leucovorin) for earlier stage colorectal cancer and for the treatment of other malignancies such as lung and pancreatic cancer.

The toxicity inherent in camptothecins limits the dosage of drug that can be administered to patients. For example, certain adverse events such as diarrhea, nausea and vomiting occur more commonly in patients on irinotecan and 5FU/leucovorin than in patients given 5FU/leucovorin alone. In addition, drug resistance can develop in cells that are repeatedly exposed to the drug. These effects limit the therapeutic effectiveness of camptothecins. Consequently, camptothecin formulations are needed that minimize their toxicity and their toxicity and their tendency to induce cellular multidrug resistance. The present invention provides such a composition and methods. These and other advantages of the present invention, as well as additional inventive features, will be apparent from the description of the invention provided herein.

SUMMARY OF THE INVENTION

The present invention is for novel camptothecin compositions, including irinotecan compositions, their preparation methods, and their use in treating proliferative diseases such as cancer, particularly in mammals, especially in humans. The compositions of the present invention include liposome-entrapped camptothecin molecules in which the liposome can contain any of a variety of neutral or charged liposome-forming materials and cardiolipin. The liposome-forming material is an amphiphilic molecule such as phosphatidyl choline, cholesterol, dipalmitoyl phosphatidyl choline, phosphatidyl serine, and the like. The cardiolipin in the liposomes can be derived from natural sources or synthetic. Depending on their composition, the liposomes can carry net negative or positive charges or can be neutral. Preferred liposomes also contain α-tocopherol.

The liposomal compositions can be used advantageously in conjunction with secondary therapeutic agents other than camptothecins, including antineoplastic, antifungal, antibiotic among other active agents, particularly cisplatin, 5-fluorouracil, leucovorin, and their mixtures. The liposomes can be multilamellar vesicles, unilamellar vesicles, or their mixtures as desired. The invention specifically contemplates methods in which a therapeutically effective amount of the inventive liposomes in a pharmaceutically acceptable excipient are administered to a mammal, such as a human.

DETAILED DESCRIPTION OF THE PREFERRED EMBODIMENTS

The present invention provides a composition and method for delivering camptothecins such as irinotecan to a mammalian host. The composition and method are characterized by 1) avoidance of solubility problems, 2) high drug and liposome stability, 3) ability to administer drug as a bolus or short infusion in a high concentration, 4) reduced drug toxicity 5) increased therapeutic efficacy of the drug, and 6) modulation of multidrug resistance in cancer cells.

The inventive composition is a liposome-entrapped camptothecin in which the liposome also contains cardiolipin. Generally, the liposomes can be formed by known techniques. For example, in one preferred technique irinotecan is dissolved in a hydrophobic solvent with cardiolipin and the cardiolipin allowed to form complexes with irinotecan. The cardiolipin/irinotecan-containing mixture can be evaporated to form a film in order to facilitate complex formation. Thereafter, solutions containing any desired additional lipophilic ingredients can be added to the film and the irinotecan/cardiolipin complexes dissolved or thoroughly dispersed in the solution. The solution can then be evaporated to form a second lipid film. A polar solvent such as an aqueous solvent can then be added to the lipid film and the resulting mixture vigorously homogenized to produce the present inventive liposomes.

Alternatively, all of the lipophilic ingredients can be dissolved in a suitable solvent that can then be evaporated to form a lipophilic film. A polar solvent such as an aqueous solvent can then be added to the lipid film and the resulting mixture vigorously homogenized to produce the present inventive liposomes.

Where the irinotecan is dissolved in the lipid film as described above the dosage form can be conveniently packaged in a single vial to which a suitable aqueous solution can be added to form the liposomes. Alternatively, a two vial system can be prepared in which the lipophilic ingredients are contained as a film in one vial and aqueous ingredients containing irinotecan are provided in a second vial. The aqueous irinotecan-containing ingredients can be transferred to the vial containing the lipid film and the liposomes formed by standard methods.

In a preferred embodiment, the liposomes, once formed, can be filtered through suitable filters to control their size distribution. Suitable filters include those that can be used to obtain the desired size range of liposomes from a filtrate. For example, the liposomes can be formed and thereafter filtered through a 5 micron filter to obtain liposomes having a diameter of about 5 microns or less. Alternatively, 1 μm, 500 nm, 100 nm or other filters can be used to obtain liposomes having diameters of about 1 μm, 500 nm, 100 nm or any suitable size range, respectively.

In accordance with the invention irinotecan is dissolved in a suitable solvent. Suitable solvents are those in which irinotecan is soluble and which can be evaporated without leaving a pharmaceutically unacceptable residue. For example, non-polar or slightly polar solvents can be used, such as ethanol, methanol, chloroform, or acetone.

Any suitable cardiolipin preparation can be used in the present invention. For example, cardiolipin can be purified from natural sources or can be chemically synthesized, such as tetramyristylcardiolipin, by such methods as are known in the art. Cardiolipin can be dissolved in a suitable solvent as described above for irinotecan and the solutions mixed or the cardiolipin can be dissolved directly with irinotecan.

Any suitable liposome-forming material can be used in the present liposomes. Suitable liposome forming materials include synthetic, semi-synthetic (modified natural) or naturally occurring compounds having a water-soluble, hydrophilic portion and a water-insoluble, hydrophobic portion. Such compounds are amphiphilic molecules and can have net positive, negative, or neutral charges. The hydrophobic portion of liposome forming compounds can include one or more nonpolar, aliphatic chains, for example, palmitoyl groups. Examples of suitable liposome-forming compounds include phospholipids, sterols, fatty acids, and the like. Preferred liposome forming compounds include cardiolipin, phosphatidyl choline, cholesterol, dipalmitoyl phosphatidyl choline, phosphatidyl serine, and α-tocopherol.

As described above for cardiolipin and irinotecan, the liposome-forming material can be dissolved in a suitable solvent, which can be a low polarity solvent such as chloroform, or a non-polar solvent, such as n-hexane. Other lipophilic ingredients can be admixed with the aforementioned ingredients, the ingredients can then be mixed with irinotecan and the solvent evaporated to produce a homogeneous lipid film. Solvent evaporation can be by any suitable means that preserves the stability of irinotecan and other lipophilic ingredients.

Liposomes can then be formed by adding a polar solution, preferably an aqueous solution, such as a saline solution, to the lipid film and dispersing the film by vigorous mixing. Optionally, the polar solution can contain irinotecan. The solution can be pure water or it can contain salts, buffers, or other soluble active agents. Any method of mixing can be used provided that the chosen method induces sufficient shearing forces between the lipid film and polar solvent to strongly homogenize the mixture and form liposomes. For example, mixing can be by vortexing, magnetic stirring, and/or sonicating. Multilamellar liposomes can be formed simply by vortexing the solution. Where unilamellar liposomes are desired a sonication or filtration step is included in the process.

More generally, any suitable method of forming liposomes can be used so long as it provides liposome entrapped irinotecan. Thus, solvent evaporation methods that do not involve formation of a dry lipid film can be used. For example, liposomes can be prepared by forming an emulsion in an aqueous and organic phase and evaporating the organic solvent. The present invention is intended to encompass liposome-entrapped irinotecan, without regard to the procedure for making the liposomes.

Suitable liposomes can be neutral, negatively, or positively charged, the charge being a function of the charge of the liposome components and pH of the liposome solution. For example, at neutral pH, positively charged liposomes can be formed from a mixture of phosphatidyl choline, cholesterol and stearyl amine. Alternatively, negatively charged liposomes can be formed from phosphatidyl choline, cholesterol, and phosphatidyl serine.

The preferred liposome entrapped irinotecan composition contains suitable amounts of irinotecan. Suitable amounts can include from 1 to 50 wt. % irinotecan, and more preferably 2 to 25 wt. % irinotecan. Preferred compositions also contain cardiolipin, cholesterol, phosphatidyl choline and α-tocopherol in suitable amounts. The inventive compositions can contain any suitable amount of cardiolipin. Suitable amounts can include from 1 to 50 wt. % cardiolipin, and more preferably 2 to 25 wt. % cardiolipin. The inventive compositions can contain any suitable amount of phosphatidylcholine. Suitable amounts of phosphatidyl choline can include from 1 to 95 wt. % phosphatidyl choline, and more preferably 20 to 75 wt. % phosphatidyl choline. Preferred liposomes of the present invention also contain suitable amounts of α-tocopherol or other suitable antioxidants. Suitable amounts range from 0.001 wt. % to 5 wt. % α-tocopherol. For reference, wt. % refers to the relative mass of each ingredient in the final composition without regard to the amount of added water.

The invention includes pharmaceutical preparations which in addition to non-toxic, inert pharmaceutically suitable excipients contain the liposome-entrapped irinotecan and processes for the production of these preparations.

The invention also includes pharmaceutical preparations in dosage units. This means that the preparations are in the form of individual parts, for example capsules, pills, suppositories and ampoules, of which the content of liposome entrapped irinotecan corresponds to a fraction or a multiple of an individual dose. The dosage units can contain, for example, 1, 2, 3 or 4 individual doses or ½, ⅓ or ¼ of an individual dose. An individual dose preferably contains the amount of irinotecan which is given in one administration and which usually corresponds to a whole, a half or a third or a quarter of a daily dose.

By non-toxic, inert pharmaceutically suitable excipients there are to be understood solid, semi-solid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays can be suitable pharmaceutical preparations.

Suppositories can contain, in addition to the liposome-entrapped irinotecan, suitable water-soluble or water-insoluble excipients. Suitable excipients are those in which the inventive liposomal entrapped irinotecan are sufficiently stable to allow for therapeutic use, for example polyethylene glycols, certain fats, and esters or mixtures of these substances.

Ointments, pastes, creams and gels can contain suitable excipients in which the liposome-entrapped irinotecan is stable and can contain eucalyptus oil, and sweeteners, for example saccharin.

The irinotecan should preferably be present in the above-mentioned pharmaceutical preparations in a concentration of about 0.1 to 50, preferably of about 0.5 to 25, percent by weight of the total mixture.

The abovementioned pharmaceutical preparations are manufactured in the usual manner according to known methods, for example by mixing the liposome-entrapped irinotecan with the excipient or excipients.

The present invention also includes the use of the active compound according to the invention and of pharmaceutical preparations which contain the active compound according to the invention in human and veterinary medicine for the prevention, amelioration and/or cure of diseases, in particular those diseases caused by cellular proliferation, such as cancer, in any mammal, such as a cow, horse, pig, dog or cat. For example, dog lymphoma can be treated effectively with the present irinotecan formulation. However, the present formulation is particularly preferred for use in the treatment of human patients, particularly for cancer and other diseases caused by cellular proliferation. The inventive compositions have particular use in treating human lymphoma, ovarian, breast, lung and colon cancers.

The active compound or its pharmaceutical preparations can be administered locally, orally, parenterally, intraperitoneally and/or rectally, preferably parenterally, especially intravenously.

In a human of about 70 kg body weight, for example, from about 0.5–5.0 mg irinotecan per kg of body weight can be administered. Preferably, about 1.0–3.0 mg of irinotecan per kg of body weight is administered. However, it can be necessary to deviate from the dosages mentioned and in particular to do so as a function of the nature and body weight of the subject to be treated, the nature and the severity of the illness, the nature of the preparation and if the administration of the medicine, and the time or interval over which the administration takes place. Thus it can suffice in some cases to manage with less that the abovementioned amount of active compound whilst in other cases the abovementioned amount of active compound must be exceeded. The particular required optimum dosage and the type of administration of the irinotecan can be determined by one skilled in the art, by available methods. Suitable amounts are therapeutically effective amounts that do not have excessive toxicity, as determined in empirical studies.

One significant advantage of the present composition is that it provides a method of modulating multidrug resistance in cancer cells that are subjected to irinotecan. In particular, the present liposomal compositions reduce the tendency of cancer cells subjected to chemotherapy with irinotecan to develop resistance thereto, and reduces the tendency of treated cells of developing resistance to other therapeutic agents, such as camptothecin, taxol, or doxorubicin, for example. Thus, other agents can be advantageously employed with the present treatment either in the form of a combination active with irinotecan or by separate administration. Of course the invention is not intended to be limited to formulations of irinotecan and other interchangeable camptothecin molecules can be used in its place.

Another advantage of the present invention is that approximately 3-fold less irinotecan accumulates in cardiac tissue as compared to conventional irinotecan. In addition, the area under the irinotecan plasma concentration curve is 200-fold higher than with the conventional irinotecan formulation. The plasma half-life of the inventive composition is approximately 10-fold greater than with the conventional irinotecan formulation.

Having described the present invention it will be apparent that one skilled in the art can make many changes and modifications to the above-described embodiments without departing from the spirit and scope of the present invention.

What is claimed is:

1. A method of treating a cellular proliferative disease, comprising administering to a mammalian host a pharmaceutical composition comprising:
   (a) a therapeutically effective amount of liposomal entrapped irinotecan also comprising cardiolipin, and
   (b) a pharmaceutically acceptable exipient, wherein at least a portion of irinotecan is complexed with cardiolipin.

2. The method of claim 1, wherein said mammalian host is a human.

3. The method of claim 1, wherein said cardiolipin is selected from a group consisting of natural cardiolipin and synthetic cardiolipin.

4. The method of claim 1, wherein said liposome bears a negative charge.

5. The method of claim 1, wherein said liposome bears a positive charge.

6. A therapeutic composition comprising liposome entrapped irinotecan, wherein said liposome comprises a first liposome forming material comprising cardiolipin and a second liposome forming material and wherein the composition comprises about 1 wt. % to about 50 wt. % irinotecan, about 1 wt. % to about 50 wt. % cardiolipin, about 1 wt. % to about 95 wt. % phosphatidylcholine, and about 0.001 wt. % to about 5 wt % α-tocopherol.

7. The composition of claim 6, wherein a portion of said cardiolipin is complexed with irinotecan.

8. The composition of claim 6, wherein said liposome entrapped irinotecan comprises vesicles having a size of about 5 μm or less.

9. The composition of claim 6, wherein said liposome entrapped irinotecan comprises vesicles having a size of about 1 μm or less.

10. The composition of claim 6, wherein said liposome entrapped irinotecan comprises vesicles having a size of about 0.5 μm or less.

11. The composition of claim 6, wherein said liposome entrapped irinotecan comprises vesicles having a size of about 0.1 μm or less.

12. The composition of claim 6, wherein said second liposome-forming material is a lipid selected from a group consisting of phosphatidyicholine, cholesterol, α-tocopherol, dipalmitoyl phosphatidylcholine and phosphatidylserine.

13. The composition of claim 6, wherein said cardiolipin is selected from a group consisting of natural cardiolipin and synthetic cardiolipin.

14. The composition of claim 6, wherein said liposome bears a negative charge.

15. The composition of claim 6, wherein said liposome bears a positive charge.

16. The composition of claim 6, wherein said liposome is neutral.

17. A method for the treatment of mammalian cancer comprising administering a therapeutically effective amount of the composition of claim 6 to a subject in need thereof.

18. The method of claim 1, wherein the composition is administered at a dosage of about 0.5–3.0 mg irinotecan per kg body weight of the host.

19. The method of claim 1, wherein the composition is administered at a dosage of about 1.0–3.0 mg irinotecan per kg body weight of the host.

20. The method of claim 1 wherein the liposomal entrapped irinotecan comprises vesicles having a size of less than about 5 μm.

21. The method of claim 1 wherein the liposomal entrapped irinotecan comprises vesicles having a size of about 1 μm or less.

22. The method of claim 1 wherein the liposomal entrapped irinotecan comprises vesicles having a size of about 0.5 μm or less.

23. The method of claim 1 wherein the liposomal entrapped irinotecan comprises vesicles having a size of about 0.1 μm or less.

24. The method of claim 1 wherein the composition comprises about 1 wt. % to about 50 wt. % irinotecan, about 1 wt. % to about 50 wt. % cardiolipin, about 1 wt. % to about 95 wt. % phosphatidyicholine, and about 0.001 wt. % to about 5 wt. % α-tocopherol.

* * * * *